United States Patent [19]  [11] 3,956,225
Murato et al.  [45] May 11, 1976

[54] STABLE DISPERSION OF VINYL POLYMER
[75] Inventors: Koichiro Murato; Minoru Shibata; Tadashi Watanabe, all of Hiratsuka, Japan
[73] Assignee: Kansai Paint Co., Ltd., Japan
[22] Filed: July 13, 1973
[21] Appl. No.: 379,053

[30] Foreign Application Priority Data
July 20, 1972 Japan.............................. 47-72002

[52] U.S. Cl. .................. 260/33.6 UA; 260/34.2; 260/885; 526/263; 526/304; 526/324; 526/342; 526/347; 526/11.1
[51] Int. Cl.² ..................... C08J 3/08; C08K 5/01; C08L 23/00
[58] Field of Search...... 260/33.6 UA, 34.2, 78.4 D, 260/78.5 R, 885

[56] References Cited
UNITED STATES PATENTS
| | | | |
|---|---|---|---|
| 3,317,635 | 5/1967 | Osmond | 260/34.2 |
| 3,505,268 | 4/1970 | Backhouse et al. | 260/34.2 |
| 3,531,440 | 9/1970 | Mehmedbasich et al. | 260/78.4 D |
| 3,607,821 | 9/1971 | Clarke et al. | 260/33.6 UA |
| 3,745,137 | 7/1973 | Reid et al. | 260/33.6 UA |
| 3,795,649 | 3/1974 | May | 260/33.6 UA |

*Primary Examiner*—Allan Lieberman
*Attorney, Agent, or Firm*—Ostrolenk, Faber, Gerb & Soffen

[57] ABSTRACT

A stable dispersion of vinyl polymer dispersed in an organic dispersion medium, said dispersed vinyl polymer being prepared from a vinyl monomer in said dispersion medium in the presence of a dispersion stabilizer which is soluble in said dispersion medium, and said dispersion stabilizer being a copolymer having comb structure which is obtained by copolymerization of vinyl monomer and aliphatic chain monomer in a solvent, further said aliphatic chain monomer being prepared by half-esterification between an alkyl succinic anhydride and a hydroxyalkyl ester of acrylic acid or methacrylic acid.

10 Claims, No Drawings

STABLE DISPERSION OF VINYL POLYMER

This invention relates to a stable dispersion of vinyl polymer which is dispersed in an organic liquid medium containing a copolymer having comb structure as a dispersion stabilizer.

In a dispersion of vinyl polymer in an organic liquid medium, the dispersion stabilizer plays an important part in the dispersion.

A dispersion containing a graft-copolymer as the dispersion stabilizer, in which the graft-copolymer is prepared from a polymerizable component which forms a solvate with the organic dispersion medium and another polymerizable component which has a different polarity from the component and hardly forms a solvate with the organic dispersion medium and joins with the dispersed particles of vinyl polymer, is well known.

As for a concrete example in the prior art which is disclosed in Japanese Patent No. 16147 of 1968, a graft-copolymer having comb structure was prepared by producing a condensation product of 12-hydroxystearic acid, then adding glycidyl methacrylate or the like by esterification of terminal free carboxyl groups to form a soluble component having unsaturated end groups, and copolymerizing a joint component such as methyl methacrylate to the reaction product. In the condensation of 12-hydroxystearic acid, however, the reactivity is low and the reaction takes a long period of time because the hydroxyl group in the 12-hydroxystearic acid is secondary. Further, when the glycidyl methacrylate is added by esterification to the terminal carboxyl group of the condensation product, the reaction temperature must be made as high as 150°C even in the presence of an esterification catalyst. In addition, there is a fear of the occurrence of polymerization between the unsaturated groups under such high temperature conditions. Still further, the condensation product of 12-hydroxystearic acid has ester bonds in its main carbon chains, so that the solubility against the organic dispersion medium mainly consisting of aliphatic hydrocarbons is restricted; accordingly, the effect as dispersion stabilizer is limited to some extent. Furthermore, in some cases, the obtained graft-copolymer having comb structure is added with auxiliary reactive groups such as unsaturated groups. In this case, troublesome measures have been taken in the conventional art, where, for example, methyl methacrylate and methacrylic acid being copolymerized as the graft-components, and the free carboxyl group of the copolymer chain being then reacted with glycidyl methacrylate by esterification, thereby introducing the unsaturated group.

In contrast with the above, according to the present invention, the above-mentioned disadvantages have been completely eliminated. That is, in the present invention, vinyl monomer is polymerized in an organic dispersion medium in the presence of a dispersion stabilizer which being soluble in the organic dispersion medium, and the organic dispersion medium mainly consists of aliphatic hydrocarbon solvents which dissolve the vinyl monomer and do not dissolve the polymerization product obtained from the vinyl monomer, in which the invention is characterized in that the dispersion stabilizer is a copolymer having comb structure which is obtained by copolymerization, in an organic solvent, of vinyl monomer and aliphatic chain monomer prepared by half-esterification of alkyl succinic anhydride which is represented by the general formula:

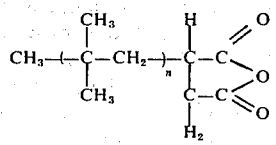

in which $n$ is an integer from 6 to 70, inclusive, and hydroxyalkyl ester of acrylic acid or methacrylic acid which is represented by the general formula:

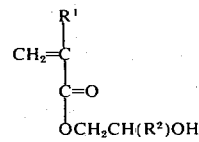

in which $R^1$ is a hydrogen atom or a methyl group, $R^2$ is a hydrogen atom or an alkyl group having 1 to 3 carbon atoms.

The half-esterification for obtaining the aliphatic chain monomer which is used for preparing said dispersion stabilizer can be carried out in a short period of time and at a relatively low temperature. In the half-esterification, 0.8 to 1.2 mols, preferably 1 mol, of hydroxyalkyl ester of acrylic acid or methacrylic acid is used per 1 mol of alkyl succinic anhydride, and the reaction is carried out at a temperature of 60° to 150°C for 30 minutes to 5 hours, with a range of 100° to 120°C for 1 to 2 hours being preferable.

As the hydroxy esters of acrylic acid and methacrylic acid, there are 2-hydroxyethyl acrylate, 2-hydroxypropyl acrylate, 2-hydroxybutyl acrylate, 2-hydroxyethyl methacrylate, 2-hydroxypropyl methacrylate, and 2-hydroxybutyl methacrylate.

As disclosed in the above, the aliphatic chain monomer of the invention can be obtained at a low temperature and in a short period of time, so that the introduced unsaturated groups are stable and copolymerization between the unsaturated groups is not caused. Further, the alkyl succinic anhydride almost consists of hydrocarbons, and accordingly, the solubility of aliphatic chain monomer in the organic dispersion medium mainly comprising aliphatic hydrocarbon solvents is excellent, and the stability of dispersoid can be thereby improved very much.

Further, there exist free carboxyl groups in the aliphatic chain monomer being produced through the half-esterification, and therefore, it is not necessary to introduce free carboxyl groups into the copolymer chains by copolymerizing acrylic acid or methacrylic acid together with methyl methacrylate during the preparation of the copolymer, as necessary in the conventional method.

The aliphatic chain monomer is then copolymerized with vinyl monomer in the solvent to obtain a copolymer having comb structure.

The ratio of the aliphatic chain monomer and vinyl monomer used is such that 100 parts by weight of the former is used to 50 to 200 parts by weight of the latter, and 100 parts by weight of the former is caused to copolymerize with preferably 80 to 120 parts by weight of the latter. The copolymerization is generally carried out by radical solution polymerization in the presence of a polymerization initiator. In this reaction, there is no limitation with regard to the solvent, that is, one or a mixture of solvents, for example, hydrocarbon solvents such as hexane and toluene, alcohols such as butanol, ketones such as methyl ethyl ketone, esters such as ethyl acetate, ethers such as dioxane, and Cellosolves such as butyl Cellosolve, may be used. When the above-mentioned solvent or solvents are used for the copolymerization, the ratio of copolymerization components is made in a range of 20 to 30 % by weight in the solvent.

The polymerization temperature is usually 60° to 150°C, and especially, the range of 80° to 120°C is preferably employed. In the process of copolymerization, which will be explained in detail in the following preparation examples, the solvent is fed into a reaction vessel, a mixture of copolymerization components and polymerization initiator is then added dropwise thereinto in the course of 1 to 4 hours at a temperature of 80° to 120°C, and thereafter the reaction is continued for a further 2 to 6 hours. During this time, it is advisable to add an additional amount of the polymerization initiator in order to improve the polymerization. In the above reaction, the suitable amount of the polymerization initiator is 0.5 to 5.0 parts by weight per 100 parts by weight of the monomer components.

As for the vinyl monomer in the copolymerization, for example, (1) styrene and its derivatives, (2) acrylic or methacrylic monomers, and (3) vinyl or vinylidene monomers may be used.

As styrene and its derivatives (1), there are styrene, vinyltoluene, 2-methylstyrene and chlorostyrene; as the acrylic or methacrylic monomer (2), there are acrylic acid, methacrylic acid, methyl methacrylate, n-butyl acrylate, n-butyl methacrylate, 2-ethylhexyl acrylate, 2-ethylhexyl methacrylate, n-octyl acrylate, n-octyl methacrylate, lauryl methacrylate, 2-hydroxyethyl acrylate, 2-hydroxyethyl methacrylate, 2-hydroxypropyl acrylate, 2-hydroxypropyl methacrylate, glycidyl acrylate, glycidyl methacrylate, dimethylaminomethyl acrylate, dimethylaminoethyl methacrylate, diethylaminoethyl acrylate and diethylaminoethyl methacrylate; and as vinyl or vinylidene monomers (3), there are acrylonitrile, vinyl acetate, vinylidene chloride, isobutyl vinyl ether, 2-vinylpyridine and diacetone acrylamide. These monomers can be used either alone or in a mixture of two or more of them.

As for polymerization initiator, commonly known radical polymerization initiators may be used, and there are, for example, azo initiators such as azobisisobutyronitrile, azobisdimethylvaleronitrile and azobiscyclohexane carbonitrile; peroxides such as benzoyl peroxide, lauroyl peroxide, di-$t$-butyl peroxide, $t$-butyl hydroperoxide, cumene hydroperoxide, $t$-butyl peroxy benzoate and $t$-butyl peroxy maleate; and organic redox initiators such as peroxide-amines.

The thus obtained solution of graft-copolymer having comb structure can be used as an excellent dispersion stabilizer to stabilize various dispersions.

As disclosed in the above, free carboxy groups are contained in the copolymer, so that, if desired, unsaturated groups can be introduced by adding glycidyl acrylate or glycidyl methacrylate through the ordinarily known esterification method. When this reaction product is used as the dispersion stabilizer, a further stable dispersion can be prepared. The reason for this fact is not definite yet. It is considered, however, that the stability of the dispersion depends upon the copolymerization between the unsaturated groups of dispersoid and the unsaturated groups of the dispersion stabilizer.

In the process of preparing the dispersion, 5 to 30 % by weight of the dispersion stabilizer against the total resin content of dispersion is used. The dispersion itself may be prepared according to the commonly known method. That is, a stable dispersion is prepared by mixing or dropping the mixture of radical polymerization initiator and vinyl monomer into the reaction medium containing aliphatic hydrocarbon solvents and the solution of dispersion stabilizer of the present invention.

As for the radical polymerization initiators used in the preparation of the dispersion, the same polymerization initiators as stated with regard to the above-mentioned preparation of the dispersion stabilizer may be used. And, as for the aliphatic hydrocarbon solvents, those having the boiling point of 30° to 300°C may be used. That is, one or a mixture of mineral spirits, kerosene oil, petroleum ether, petroleum benzin, gasoline, cyclohexane, $n$-hexane, iso-octane, $n$-octane, naphtha, dipentene, isodecane, pentane, heptane and the like can be used.

In the following, the present invention will be further explained in detail according to several examples, in which the amount of materials are represented in parts by weight unless otherwise indicated. Further, the present invention is by no means restricted to such examples.

PREPARATION EXAMPLES OF DISPERSION STABILIZERS

Preparation Example 1 a. A reaction vessel with a thermometer, a stirrer and a gas inlet pipe was fed with 1 mol of alkyl succinic anhydride of 500 in average molecular weight and 1 mol of 2-hydroxyethyl methacrylate, and further fed with mineral spirits to form a 50 % solution of the above materials. Then, under a nitrogen gas current, the above solution was caused to react for 3 hours at 80°C with agitation. Thereby, a half-esterification product (50 % mineral spirits solution) of the above alkyl succinic anhydride and 2-hydroxyethyl methacrylate was obtained.

b. In the next step, a reaction vessel with a thermometer, a stirrer, a reflux condenser, a dropping funnel and a gas inlet pipe was fed with 100 parts of mineral spirits and heated to 110°C under nitrogen gas current. Then, a mixture of the above obtained half-esterification product (50 % solution) in the amount of 200 parts, 100 parts of methyl methacrylate and 3 parts of benzoyl peroxide was added dropwise for 2 hours, the contents being kept at 110°C. After the dropping of the mixture, the reaction was further continued for 3 hours at 110°C. Through the above steps, a dispersion stabilizer (50 % mineral spirit solution) having comb type structure was obtained.

PREPARATION EXAMPLES 2 TO 5

The Preparation Examples 2 to 4 were carried out in like manner as the above-mentioned Preparation Example 1. In Preparation Examples 3 and 4, a small amount of polymerization inhibitor was added in each half-esterification step.

The conditions for the half-esterification and the copolymerization are shown in the following Tables 1 and 2.

EXAMPLES FOR PREPARATION OF VINYL POLYMER DISPERSION

Table 1.

| Preparation Example | Alkyl Succinic Anhydride | Hydroxyalkyl Ester of Acrylic Acid or Methacrylic Acid | Half-Esterification Solvent[*1] | Polymerization Inhibitor | Reaction Temperature (°C) | Reaction Time (hours) |
| --- | --- | --- | --- | --- | --- | --- |
| 2-(a) | Average M.W.=1,000 1 mol | 2-hydroxyethyl acrylate: 1 mol | Mixture of mineral spirits/ butyl acetate = 70/30 | None | 100 | 2 |
| 3-(a) | Average M.W.=2,000 1 mol | Hydroxypropyl methacrylate: 1.1 mol | Mineral spirits | Hydroquinone: 300 ppm | 120 | 2 |
| 4-(a) | Average M.W.=3,000 1 mol | Hydroxypropyl acrylate 1.2 mol | Mineral spirits | Hydroquinone: 300 ppm | 140 | 2 |
| 5-(a) | Average M.W.=1,500 1 mol | 2-hydroxyethyl acrylate: 0.8 mol | Mixture of mineral spirits/ butyl acetate = 90/10 | Hydroquinone: 300 ppm | 120 | 2 |

Note: [*1] The solvents were added so as to form each 50 % solution of the mixture of alkyl succinic anhydride and hydroxyalkyl acrylate or hydroxyalkyl methacrylate.

Table 2

| Preparation Example | In Reaction Vessel | Copolymerization In Dropping Funnel | Reaction Temperature | Dropping Time of Vinyl Monomer (hours) | Reaction Time after Dropping of Vinyl Monomer (hours) | Solid Content of Obtained Dispersion Stabilizer |
| --- | --- | --- | --- | --- | --- | --- |
| 2-(b) | Mineral spirits: 100 parts | 2-(a): 200 parts, Methyl methacrylate: 100 parts, and Azobisisobutyronitrile: 4 parts | 90 | 3 | 2 | 50 % |
| 3-(b) | Mineral spirits: 110 parts | 3-(a): 180 parts, Methyl methacrylate: 100 parts, n-Butyl acrylate: 10 parts, and Benzoyl peroxide: 4 parts | 100 | 2 | 3 | 50 % |
| 4-(b) | Mineral spirits: 90 parts | 4-(a): 220 parts, Methyl methacrylate: 70 parts, Ethyl acrylate: 20 parts, and azobisisobutyronitrile: 2 parts | 120 | 4 | 2 | 50 % |
| 5-(b) | Mineral spirits: 40 parts | 5-(a): 160 parts, Methyl methacrylate: 80 parts, and lauryl methacrylate: 20 parts | 120 | 5 | 1 | 60 % |

PREPARATION EXAMPLE 6

In the same reaction vessel as that of the above Preparation Example 1-(b), 100 parts of the product (50 % solution) obtained in Preparation Example 2-(b), 4 parts of glycidyl methacrylate, and 0.2 parts of triethyl amine were introduced, and the contents were caused to react at 120°C until the acid value of reaction product became 0.3. Through this reaction, the ester addition is caused between free carboxyl groups of alkyl succinic anhydride and epoxy groups of glycidyl methacrylate, so that a small amount of unsaturated vinyl groups is introduced to the dispersion stabilizer.

EXAMPLE 1

A reaction vessel with a thermometer, a reflux condenser, a stirrer and a gas inlet pipe is fed with 20 parts of the dispersion stabilizer solution prepared in Preparation Example 1-(b), 90 parts of methyl methacrylate, 90 parts of mineral spirits, 200 parts of petroleum benzin and 1.5 parts of benzoyl peroxide, which were caused to react for 3 hours at 75°C in nitrogen gas atmosphere. Thereafter, 150 parts of the petroleum benzin was removed by evaporation through heating at atmospheric pressure for 2 hours. The temperature of the reaction mixture after 2 hours was 110°C. Thus, a stable dispersion of thermoplastic polymer having a resin content of 40 % was obtained. This dispersion was then applied on the surface of a glass plate and baked for 20 minutes at 160°C, and thereby a smooth and transparent coating film was formed.

EXAMPLE 2

The same reaction vessel as that in Example 1 was fed with 30 parts of the dispersion stabilizer solution obtained in Preparation Example 2-(b), 50 parts of n-heptane and 50 parts of aliphatic hydrocarbon having a boiling point of 120° to 140°C. Then, in the nitrogen gas atmosphere, a mixture of 90 parts of methyl methacrylate, 10 parts of n-butyl acrylate and 2 parts of azobisisobutyronitrile was added dropwise from the dropping funnel in the course of 2 hours at 85°C. Thereafter, the reaction was further continued for 3 hours at the same temperature. As the result of this reaction, a stable dispersion of thermoplastic polymer having resin content of 50 % was obtained.

This dispersion was applied on the surface of glass plate and was heated at 150°C for 30 minutes, and thereby a smooth and transparent coating film was formed on the substrate.

EXAMPLE 3

The same reaction vessel as that in Example 1 was fed with 50 parts of cyclohexane and 50 parts of mineral spirits; then, in the nitrogen gas atmosphere, a mixture of 40 parts of the dispersion stabilizer solution obtained in Preparation Example 3-(b), 80 parts of methyl methacrylate, 20 parts of ethyl acrylate and 1.5 parts of azobisdimethyl valeronitrile was added therein in the course of 6 hours from the dropping funnel, the contents of the reaction vessel being kept at 82°C. After the dropping of the above, the reaction was further continued for 1 hour at the same temperature. As the result of this reaction, a stable dispersion of thermoplastic polymer having a resin content of 50 % was obtained.

This dispersion was then applied on the surface of a glass plate and was heated at 150°C for 30 minutes, and thereby a smooth and transparent coating film was formed on the substrate.

EXAMPLE 4

The reaction vessel used in Example 1 was fed with 100 parts of mineral spirits, and to the contents of the vessel being kept at 120°C was further added a mixture of 30 parts of dispersion stabilizer solution obtained in Preparation Example 4-(b), 30 parts of styrene, 20 parts of ethyl acrylate, 10 parts of methyl methacrylate, 23 parts of 2-ethylhexyl methacrylate, 15 parts of 2-hydroxyethyl methacrylate, 2 parts of methacrylic acid and 2parts of benzoyl peroxide from the dropping funnel in the course of 3 hours. Thereafter, the reaction was further continued for 1 hour at the same temperature. Then, 0.5 part of azobisisobutyronitrile was added into the reaction mixture, and after 1 hour of such addition, a further 0.5 part of azobisisobutyronitrile was added and the reaction was still continued for further 2 hours. As the result of this reaction, a stable dispersion of thermoplastic polymer having a resin content of 50 % was obtained.

The above dispersion in an amount of 140 parts was mixed with a condensation product of butylated melamine and formaldehyde (formaldehyde/melamine (molar ratio) = 5.6), and the obtained mixture was applied on the surface of a glass and was heated at 140°C for 30 minutes. As the result of the above heating, a smooth and transparent coating film was formed, and the film was not dissolved by acetone.

EXAMPLE 5

The same reaction vessel as used in Example 1 was fed with 100 parts of n-heptane and 16 parts of the dispersion stabilizer obtained in the foregoing Preparation Example 5-(b), and to the contents of the vessel being kept at 100°C was further added a mixture of 30 parts of styrene, 10 parts of n-butyl methacrylate, 12 parts of 2-hydroxyethyl acrylate, 15 parts of acrylonitrile, 21 parts of 2-ethylhexyl acrylate, 10 parts of methyl methacrylate, 2 parts of acrylic acid, 48 parts of the dispersion stabilizer obtained in the foregoing Preparation Example 5-(b) and 15 parts of azobisisobutyronitrile from the dropping funnel in the course of 5 hours. Thereafter, the reaction was further continued for 30 minutes at the same temperature. Then, a mixture of 2 parts of azobisisobutyronitrile and 16 parts of methyl ethyl ketone was further added from the dropping funnel in the course of 3 hours. After the dropping of the above, the reaction was further continued for 2 hours at the same temperature. As the result of the reaction, a stable dispersion of thermosetting polymer having a resin content of 50 % was obtained.

The above dispersion in an amount of 150 parts was mixed with a condensation product of butylated melamine and formaldehyde (formaldehyde/melamine (molar ratio) = 4.8). The obtained mixture was applied on the surface of a glass plate and then was heated at 140°C for 30 minutes. As the result of the above heating, a smooth and transparent coating film was formed, and the film was not dissolved with acetone.

EXAMPLE 6

The same reaction vessel as used in Example 1 was fed with 55 parts of aliphatic hydrocarbon of 120° to 140°C in boiling point and 50 parts of n-hexane, and these contents were heated up to the boiling point thereof. Then 5 parts of methyl methacrylate, 3 parts of the dispersion stabilizer obtained in the foregoing Preparation Example 6, and 0.4 part of azobisisobutyronitrile were added simultaneously into the above mixture, and the contents were caused to react for 30 minutes at the boiling point. After that, a mixture of 25 parts of styrene, 30 parts of n-butyl methacrylate, 28 parts of 2-ethylhexyl methacrylate, 15 parts of hydroxypropyl methacrylate, 2 parts of acrylic acid, 26 parts of the dispersion stabilizer solution obtained in Preparation Example 5, 1 part of n-octyl mercaptan and 1.2 parts of azobisisobutyronitrile was added from the dropping funnel in the course of 5 hours, where the contents of the reaction vessel were kept at the boiling point. After continuing the reaction for additional 1 hour at the boiling point, 0.3 part of azobisisobutyronitrile was added, and thereafter 5 doses of 0.3 part each of azobisisobutyronitrile were added at 30 minute intervals, and the reaction was then continued for further 2 hours at the boiling point. Thus, a stable dispersion of thermoplastic polymer having a resin content of 50 % was obtained.

Into this dispersion in an amount of 150 parts, a condensation product of butylated melamine and formaldehyde (formaldehyde/malamine (molar ratio) = 5.8) was mixed, and this mixture was applied on the surface of a glass plate and heated at 140°C for 30 minutes. As the result, a smooth and transparent coating film was formed on the substrate and the film was not dissolved by acetone.

What is claimed is:

1. Method for producing a stable dispersion of vinyl polymer which is characterized by the steps of:
   A. preparing aliphatic chain monomer through half-esterification between alkyl succinic anhydride and hydroxyalkyl ester of acrylic acid or methacrylic acid at a temperature of 60° to 150° C. for 30 minutes to 5 hours, and then preparing a copolymer having a comb structure through copolymerization in the presence of a polymerization initiator of 100 parts by weight of said aliphatic chain monomer and 50–200 parts by weight of vinyl monomer in a solvent, the amount of monomers in the solvent being 20–30% by weight, at a temperature of 60° to 150° C., whereby a dispersion stabilizer is obtained; and
   B. preparing said dispersion of vinyl polymer by polymerization of vinyl monomer in the presence of 5–30% by weight of the total resin content of said dispersion of the thus obtained solution of copolymer having comb structure in hydrocarbon solvent, wherein said alkyl succinic anhydride is of the formula

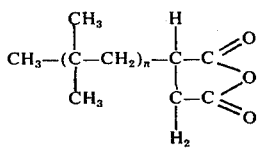

in which $n$ is an integer from 7 to 70 and said hydroxyalkyl ester is of the formula

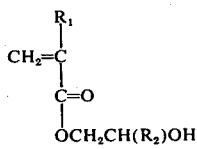

in which $R_1$ is hydrogen or methyl and $R_2$ is hydrogen or alkyl of 1 to 3 carbon atoms.

2. In a stable dispersion of vinyl polymer dispersed in an organic dispersion medium, said dispersed vinyl polymer being prepared from vinyl monomer in said dispersion medium in the presence of a dispersion stabilizer which is soluble in said dispersion medium, and said organic dispersion medium consisting essentially of aliphatic hydrocarbon solvents which dissolve said vinyl monomer but do not dissolve said vinyl polymer, the improvement which comprises using as said dispersion stabilizer, in an amount of 5–30% by weight of the total resin content of the dispersion, a copolymer having comb structure which is a copolymer of 50–200 parts by weight of vinyl monomer and 100 parts by weight of aliphatic chain monomer, said aliphatic chain monomer being the half-esterification product of alkyl succinic anhydride of the formula

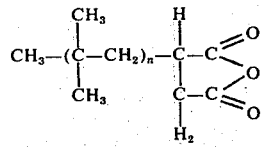

in which $n$ is an integer from 7 to 70 and a hydroxyalkyl ester of acrylic acid or methacrylic acid of the formula

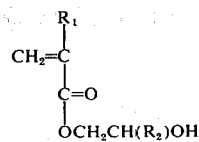

in which $R_1$ is hydrogen or methyl and $R_2$ is hydrogen or alkyl of 1 to 3 carbon atoms.

3. A stable dispersion of vinyl polymer as claimed in claim 2, in which said hydroxyalkyl ester of acrylic acid or methacrylic acid is at least one member selected from the group consisting of hydroxyethyl acrylate, hydroxypropyl acrylate, hydroxybutyl acrylate, hydroxyethyl emthacrylate, hydroxypropyl methacrylate and hydroxybutyl methacrylate.

4. A stable dispersion of vinyl polymer as claimed in claim 2, in which said vinyl monomer is at least one member selected from the group consisting of styrene, styrene derivatives, acrylic monomers, methacrylic monomers, acrylonitrile, vinyl acetate, isobutyl vinyl ether, 2-vinylpyridine, diacetone acrylamide, and vinylidene compounds.

5. A stable dispersion of vinyl polymer as claimed in claim 5 in which said vinyl monomer is at least 1 member of the group consisting of styrene, vinyl toluene, 2-methyl styrene, chlorostyrene, acrylic acid, methacrylic acid, methylmethacrylate, $n$-butyl methacrylate, 2-ethylhexyl acrylate, 2-ethylhexyl methacrylate, $n$-octyl acrylate, $n$-octyl methacrylate, lauryl methacrylate, 2-hydroxyethyl acrylate, 2-hydroxyethyl methacrylate, 2-hydroxypropyl acrylate, 2-hydroxypropyl methacrylate, glycidyl acrylate, glycidyl methacrylate, dimethylaminomethyl acrylate, dimethylaminoethyl methacrylate, diethylaminoethyl acrylate, diethylaminoethyl methacrylate, and vinylidene chloride.

6. A stable dispersion of vinyl polymer as claimed in claim 2 wherein said aliphatic chain monomer is the half-esterification product of said alkyl succinic anhydride having an average molecular weight of 500 and 2-hydroxyethyl methacrylate and said vinyl monomer copolymerized with said aliphatic chain monomer is methyl methacrylate.

7. A stable dispersion of vinyl polymer as claimed in claim 2 wherein said aliphatic chain monomer is the half-esterification product of said alkyl succinic anhydride having an average molecular weight of 1000 and 2-hydroxyethyl acrylate and said vinyl monomer copolymerized with said aliphatic chain monomer is methyl methacrylate.

8. A stable dispersion of vinyl polymer as claimed in claim 2 wherein said aliphatic chain monomer is the half-esterification product of said alkyl succinic anhydride having an average molecular weight of 2000 and 2-hydroxypropyl methacrylate and said vinyl monomer copolymerized with said aliphatic chain monomer is a mixture of methyl methacrylate and $n$-butyl methacrylate.

9. A stable dispersion of vinyl polymer as claimed in claim 2 wherein said aliphatic chain monomer is the half-esterification product of said alkyl succinic anhydride having an average molecular weight of 3000 and 2-hydroxypropyl acrylate and said vinyl monomer copolymerized with said aliphatic chain monomer is a mixture of methyl methacrylate and ethyl acrylate.

10. A stable dispersion of vinyl polymer as claimed in claim 2 wherein said aliphatic chain monomer is the half-esterification product of said alkyl succinic anhydride having an average molecular weight of 1500 and 2-hydroxyethyl acrylate and said vinyl monomer copolymerized with said aliphatic chain monomer is a mixture of methyl methacrylate and lauryl methacrylate.

* * * * *